(12) United States Patent
Ankenbauer et al.

(10) Patent No.: US 6,692,932 B1
(45) Date of Patent: Feb. 17, 2004

(54) THERMOSTABLE DNA POLYMERASE FROM ANAEROCELLUM THERMOPHILUM

(76) Inventors: Waltraud Ankenbauer, Oberanger 18, D-82377 Penzberg (DE); Gudrun Schmitz-Agheguian, Wettersteinstr. 3, D-82347 Bernried (DE); Elizaveta Bonch-Osmolovskaya, Lomonosovski Avenue 33-2-60, Moscow, 117192 (RU); Vitaly Svetlichny, Warmensteinacher Str. 91G, D-95448 Bayreuth (DE); Ursula Markau, Hungerwiese 1, D-82398 Polling (DE); Bernhard Angerer, Schützenstr. 20, D-83024 Rosenheim (DE); Astrid Reiser, Schleier-Weg 20, D-82387 Antdorf (DE)

( * ) Notice: Subject to any disclaimer, the term of this patent is extended or adjusted under 35 U.S.C. 154(b) by 0 days.

(21) Appl. No.: 09/269,858
(22) PCT Filed: Oct. 1, 1997
(86) PCT No.: PCT/EP97/05390
§ 371 (c)(1), (2), (4) Date: Jun. 10, 1999
(87) PCT Pub. No.: WO96/10640
PCT Pub. Date: Apr. 11, 1996

(30) Foreign Application Priority Data

Oct. 3, 1996 (EP) .......................................... 961158771

(51) Int. Cl.[7] .............................. C12Q 1/48; C12N 9/12
(52) U.S. Cl. ........................ 435/15; 435/194; 435/91.1; 435/91.2; 435/91.5; 536/23.2; 536/23.1
(58) Field of Search ............................ 435/91.1, 91.2, 435/91.5, 194, 15; 536/23.1, 23.2

(56) References Cited

U.S. PATENT DOCUMENTS 4,683,202 A   7/1987   Mullis .......................... 435/91

OTHER PUBLICATIONS

Bolchakova et al., Cloning and Sequence of DNA–polymerase1 Gene of Extremely Thermophilic Cellulotic Bacteruium Anaerocellum Thermophilum, EMBL Accession No: X98575, Sep. 1996.*
Bonch Osmolovskaya and Stetter, "Interspecies Hydrogen Transfer in Cocultures of Thermophilic *Archaea*", *System. Appl. Microbiology*, 1991, 14: 205–208.
Braithwaite and Ito, "Compilation, alignment, and phylogenetic relationships of DNA Polymerases", *Nucleic Acids Research*, 1993, 21: 787–802.
Brinkmann et al., "High–level expression of recombinant genes in *Escherichia coli* is dependent on the availability of the dnaY gene product", *Gene*, 1989, 85: 109–114.
Brock et al., "*Thermus aquaticus* gen. n. and sp. n., a Non–sporulating Extreme Thermophile", *Journal of Bacteriology*, 1969, 98: 289–297.

Engelke et al., Purification of *Thermus aquaticus* DNA Polymerase Expressed in *Escherichia coli* , *Analytical Biochemistry*, 1990, 191: 396–400.
Höltke et al., "Sensitive Chemiluminescent Detection of Digoxigenin–Labeled Nucleic Acids: A Fast and Simple Protocol and Its Applications", *Biotechniques*, 1992, 12: 104–113.
Kaledin et al., "Isolation and Properties of DNA Polymerase from the Extremely Thermophilic Bacterium *Thermus ruber*", *Biochemistry* (translated from Russian), 1983, 47: 1515–1521.
Kaledin et al., "Isolation and Properties of DNA Polymerase from the Extremely Thermophilic Bacterium *Thermus flavus*", *Biochemistry* (translated from Russian), 1982, 46: 1247–1254.
Kaledin et al., "Isolation and Properties of DNA Polymerase from the Extremal Thermophylic Bacteria *Thermus Aquaticus* YT–1", *Biokhimiya*, 1980, 44: 644–651.
Lawyer et al., "Isolation, Characterization and Expression in *Escherichia coli* of the DNA Polymerase Gene from *Thermus aquaticus*" *The Journal of Biological Chemistry*, 1989, 264: 6427–6437.
Lundberg et al., "High–fidelity amplification using a thermostable DNA polymerase isolated from *Pyrococcus furiosus*", *Gene*, 1991, 108: 1–6.
Neuner et al., "*Thermococcus litoralis* sp. nov.: A new species of extremely thermophilic marine archaebacteria", *Archives of Microbiology*, 1990, 153: 205–207.
Ochman et al., "Amplification of Flanking Sequences by Inverse PCR", *PCR Protocols: A Guide to Methods and Applications*, 1990, pp. 219–227.
Perler et al., "Thermostable DNA Polymerases", Advances in Protein Chemistry, 1996, 48: 377–435.
Perler et al., "Intervening sequences in an Archaea DNA polymerase gene", *Proceedings of National Academy of Science USA*, 1992, 89: 5577–5581.
Rosenberg et al., "Vectors for selective expression of cloned DNAs by T7 RNA polymerase", *Gene*, 1987, 56: 125–135.
Rüttimann et al., "DNA polymerases from the extremely thermophilic bacterium *Thermus thermophilus* HB–8", *Eur. Journal of Biochemistry*, 1985, 149: 41–46.

(List continued on next page.)

*Primary Examiner*—Rebecca E. Prouty
*Assistant Examiner*—Richard Hutson
(74) *Attorney, Agent, or Firm*—Pennie & Edmonds LLP

(57) ABSTRACT

A thermostable enzyme is provided which is derived from the microorganism *Anaerocellum thermophilum*[t]. The enzyme has a molecular weight of 96 to 100 kDa, shows DNA polymerase activity and reverse transcriptase activity in the presence of magnesium ions. The enzyme may be native or recombinant, and may be used with selected primers and nucleoside triphosphates in a temperature cycling polymerase chain reaction on DNA or RNA as template with or without additional DNA polymerases as an enzyme mixture.

3 Claims, 9 Drawing Sheets

OTHER PUBLICATIONS

Studier et al., "Use of T7 RNA Polymerase to Direct Expression of Cloned Genes", *Methods in Enzymology,* 1990, 185: 60–89.

Svetlichny et al., "*Carboxydothermus hydrogenoformans* gen. nov., sp. nov., a CO–utilitizing Thermophilic Anaerobic Bacterium from Hydrothermal Environments of Kunashir Island", *System. Appl. Microbiology,* 1991, 14: 254–260.

Svetlichny et al., "An *Aerocellum thermophilum* gen. nov. sp. nov., An Extreme Thermophilic Celluloselytic Eubacterium Isolated From Hot Springs in the Valley of Geysers", *Mikrobilogiya,* 1990, 59: 871–879.

Triglia et al., "A procedure for in vitro amplification of DNA segments that lie outside the boundaries of known sequences", *Nucleic Acids Research,* 1988, 16: 8186.

* cited by examiner

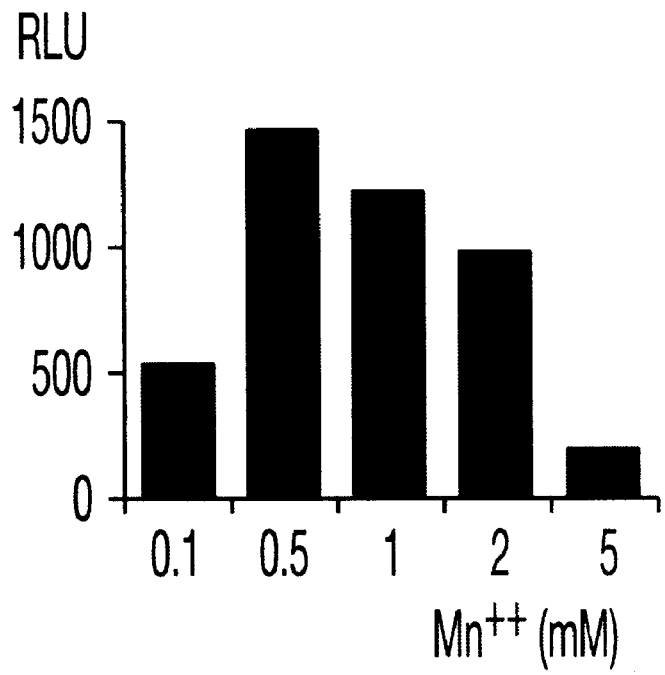
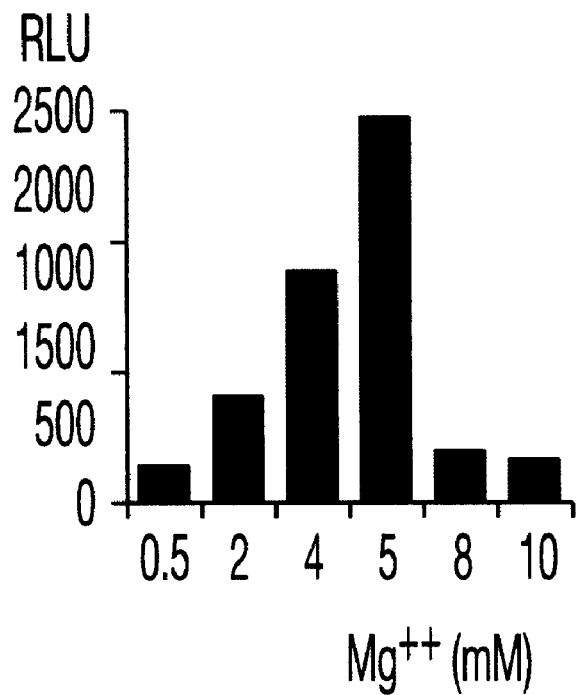
Fig. 2

SEQ ID NO: 7:
SEQ ID NO: 8:

```
ATG AAA CTG GTT ATA TTC GAT GGA AAC AGC ATT TTG TAC AGA GCC TTT    48
 M   K   L   V   I   F   D   G   N   S   I   L   Y   R   A   F    16

TTT GCT CTT CCT GAA CTG ACA ACC TCA AAT AAT ATT CCA ACA AAC GCT    96
 F   A   L   P   E   L   T   T   S   N   N   I   P   T   N   A    32

ATA TAT GGA TTT GTA AAT GTG ATA TTG AAA TAT TTA GAA CAA GAA AAA   144
 I   Y   G   F   V   N   V   I   L   K   Y   L   E   Q   E   K    48

CCT GAT TAT GTT GCT GTA GCA TTT GAT AAA AGA GGA AGA GAG GCA CGA   192
 P   D   Y   V   A   V   A   F   D   K   R   G   R   E   A   R    64

AAA AGC GAG TAC GAA GAA TAT AAA GCT AAC AGA AAA CCT ATG CCA GAT   240
 K   S   E   Y   E   E   Y   K   A   N   R   K   P   M   P   D    80

AAC CTT CAA GTA CAA ATC CCT TAT GTT CGA GAG ATT CTT TAT GCC TTT   288
 N   L   Q   V   Q   I   P   Y   V   R   E   I   L   Y   A   F    96

AAC ATT CCA ATA ATT GAG TTT GAA GGA TAT GAA GCA GAT GAT GTA ATC   336
 N   I   P   I   I   E   F   E   G   Y   E   A   D   D   V   I   112

GGT TCA CTT GTT AAC CAG TTC AAA AAT ACT GGT TTG GAT ATT GTT ATT   384
 G   S   L   V   N   Q   F   K   N   T   G   L   D   I   V   I   128

ATT ACG GGT GAC AGG GAT ACT CTT CAG TTG CTC GAC AAA AAT GTA GTT   432
 I   T   G   D   R   D   T   L   Q   L   L   D   K   N   V   V   144

GTG AAG ATT GTT TCA ACA AAA TTT GAT AAA ACA GTA GAA GAT TTG TAC   480
 V   K   I   V   S   T   K   F   D   K   T   V   E   D   L   Y   160

ACT GTG GAA AAT GTT AAA GAA AAA TAT GGG GTT TGG GCA AAT CAA GTG   528
 T   V   E   N   V   K   E   K   Y   G   V   W   A   N   Q   V   176
```

*Fig. 4*

```
CCT GAT TAC AAA GCG CTT GTT GGA GAC CAA TCA GAT AAC ATT CCC GGG   576
 P   D   Y   K   A   L   V   G   D   Q   S   D   N   I   P   G   192

GTA AAG GGA ATT GGC GAA AAG AGT GCC CAG AAG CTC TTG GAA GAG TAC   624
 V   K   G   I   G   E   K   S   A   Q   K   L   L   E   E   Y   208

TCA TCC TTA GAA GAG ATA TAC CAA AAT TTA GAT AAA ATT AAA AGT TCC   672
 S   S   L   E   E   I   Y   Q   N   L   D   K   I   K   S   S   224

ATT CGT GAA AAG TTA GAA GCA GGA AAA GAT ATG GCG TTT TTA TCC AAG   720
 I   R   E   K   L   E   A   G   K   D   M   A   F   L   S   K   240

CGC TTA GCA ACA ATT GTA TGT GAT TTA CCA CTA AAT GTT AAA CTT GAA   768
 R   L   A   T   I   V   C   D   L   P   L   N   V   K   L   E   256

GAC CTA AGA ACA AAA GAG TGG AAC AAG GAA AGG CTC TAT GAG ATT TTG   816
 D   L   R   T   K   E   W   N   K   E   R   L   Y   E   I   L   272

GTG CAG TTA GAG TTC AAA AGC ATA ATA AAA CGG TTA GGA GTT CTA TCA   864
 V   Q   L   E   F   K   S   I   I   K   R   L   G   V   L   S   288

GAA GTT CAA TTT GAA TTT GTT CAG CAG CGA ACC GAT ATA CCT GAC GTT   912
 E   V   Q   F   E   F   V   Q   Q   R   T   D   I   P   D   V   304

GAA CAA AAA GAG CTT GAA AGT ATT TCA CAA ATA AGA TCA AAA GAG ATT   960
 E   Q   K   E   L   E   S   I   S   Q   I   R   S   K   E   I   320

CCA TTA ATG TTT GTA CAG GGC GAA AAA TGT TTT TAT TTA TAT GAT CAA  1008
 P   L   M   F   V   Q   G   E   K   C   F   Y   L   Y   D   Q   336

GAA AGT AAT ACT GTA TTT ATA ACA AGT AAT AAA CTT TTG ATA GAG GAG  1056
 E   S   N   T   V   F   I   T   S   N   K   L   L   I   E   E   352
```

*Fig. 4 continued*

```
ATT TTA AAA AGT GAT ACT GTG AAA ATT ATG TAT GAT TTG AAA AAT ATA   1104
 I   L   K   S   D   T   V   K   I   M   Y   D   L   K   N   I    368

TTT CAT CAA CTC AAC CTG GAA GAC ACT AAT AAT ATT AAA AAT TGC GAA   1152
 F   H   Q   L   N   L   E   D   T   N   N   I   K   N   C   E    384

GAT GTA ATG ATT GCT TCC TAT GTT CTT GAC AGC ACA AGA AGT TCA TAT   1200
 D   V   M   I   A   S   Y   V   L   D   S   T   R   S   S   Y    400

GAG TTA GAA ACG TTG TTT GTA TCT TAC TTG AAC ACT GAC ATA GAA GCT   1248
 E   L   E   T   L   F   V   S   Y   L   N   T   D   I   E   A    416

GTA AAA AAA GAC AAG AAG ATA GTC TCT GTG GTA CTT CTA AAA CGG TTA   1296
 V   K   K   D   K   K   I   V   S   V   V   L   L   K   R   L    432

TGG GAC GAG CTT TTG AGA TTA ATA GAT TTA AAT TCA TGC CAG TTT TTA   1344
 W   D   E   L   L   R   L   I   D   L   N   S   C   Q   F   L    448

TAT GAG AAT ATA GAA AGA CCT CTT ATC CCA GTT CTA TAT GAA ATG GAA   1392
 Y   E   N   I   E   R   P   L   I   P   V   L   Y   E   M   E    464

AAA ACA GGA TTT AAG GTG GAT AGA GAT GCC CTC ATC CAA TAT ACC AAA   1440
 K   T   G   F   K   V   D   R   D   A   L   I   Q   Y   T   K    480

GAG ATT GAA AAC AAA ATA TTA AAA CTT GAA ACG CAG ATA TAC CAG ATT   1488
 E   I   E   N   K   I   L   K   L   E   T   Q   I   Y   Q   I    496

GCA GGT GAG TGG TTT AAC ATA AAT TCA CCG AAA CAG CTT TCT TAC ATT   1536
 A   G   E   W   F   N   I   N   S   P   K   Q   L   S   Y   I    512

TTG TTT GAA AAG CTA AAA CTT CCT GTA ATA AAG AAG ACA AAA ACA GGA   1584
 L   F   E   K   L   K   L   P   V   I   K   K   T   K   T   G    528

TAT TCC ACT GAT GCC GAG GTT TTA GAA GAG CTT TTT GAC AAA CAT GAA   1632
 Y   S   T   D   A   E   V   L   E   E   L   F   D   K   H   E    544
```

*Fig. 4 continued*

```
ATA GTT CCT CTT ATT TTG GAT TAC AGG ATG TAT ACA AAG ATA CTG ACA   1680
 I   V   P   L   I   L   D   Y   R   M   Y   T   K   I   L   T    560

ACT TAC TGT CAG GGA TTA CTA CAG GCA ATA AAT CCT TCT TCG GGT AGA   1728
 T   Y   C   Q   G   L   L   Q   A   I   N   P   S   S   G   R    576

GTT CAT ACA ACC TTT ATC CAA ACA GGT ACA GCC ACA GGA AGA CTT GCA   1776
 V   H   T   T   F   I   Q   T   G   T   A   T   G   R   L   A    592

AGC AGC GAT CCT AAT TTA CAA AAT ATA CCT GTA AAA TAT GAT GAG GGG   1824
 S   S   D   P   N   L   Q   N   I   P   V   K   Y   D   E   G    608

AAA TTG ATA CGA AAG GTT TTT GTA CCT GAG GGT GGA CAT GTA CTG ATT   1872
 K   L   I   R   K   V   F   V   P   E   G   G   H   V   L   I    624

GAT GCA GAT TAT TCC CAA ATT GAG CTG AGA ATA CTT GCC CAT ATT TCT   1920
 D   A   D   Y   S   Q   I   E   L   R   I   L   A   H   I   S    640

GAA GAT GAA AGA CTT ATA AGT GCT TTC AAA AAT AAT GTT GAC ATT CAT   1968
 E   D   E   R   L   I   S   A   F   K   N   N   V   D   I   H    656

TCG CAG ACA GCA GCT GAG GTT TTT GGT GTA GAC ATA GCC GAT GTT ACT   2016
 S   Q   T   A   A   E   V   F   G   V   D   I   A   D   V   T    672

CCA GAG ATG AGA AGT CAA GCT AAA GCA GTA AAT TTT GGT ATA GTT TAT   2064
 P   E   M   R   S   Q   A   K   A   V   N   F   G   I   V   Y    688

GGG ATT TCT GAT TAT GGT CTT GCA AGG GAT ATT AAA ATT TCC AGG AAA   2112
 G   I   S   D   Y   G   L   A   R   D   I   K   I   S   R   K    704

GAA GCT GCA GAG TTT ATA AAT AAG TAT TTT GAG CGT TAT CCC AAA GTT   2160
 E   A   A   E   F   I   N   K   Y   F   E   R   Y   P   K   V    720

AAA GAG TAT TTA GAT AAT ACT GTT AAG TTT GCT CGT GAT AAT GGA TTT   2208
 K   E   Y   L   D   N   T   V   K   F   A   R   D   N   G   F    736
```

*Fig. 4 continued*

```
GTT TTG ACT TTA TTT AAT AGA AAG AGA TAT ATA AAA GAC ATA AAA TCT    2256
 V   L   T   L   F   N   R   K   R   Y   I   K   D   I   K   S     752

ACA AAC AGA AAC TTA AGG GGT TAT GCA GAA AGG ATT GCA ATG AAT TCG    2304
 T   N   R   N   L   R   G   Y   A   E   R   I   A   M   N   S     768

CCA ATT CAG GGC AGT GCT GCT GAT ATC ATG AAA TTG GCA ATG ATT AAG    2352
 P   I   Q   G   S   A   A   D   I   M   K   L   A   M   I   K     784

GTT TAT CAG AAA CTT AAA GAA AAC AAT CTC AAA TCA AAA ATA ATT TTG    2400
 V   Y   Q   K   L   K   E   N   N   L   K   S   K   I   I   L     800

CAG GTA CAC GAT GAG CTT TTA ATT GAA GCC CCA TAC GAA GAA AAG GAT    2448
 Q   V   H   D   E   L   L   I   E   A   P   Y   E   E   K   D     816

ATA GTA AAG GAA ATA GTA AAA AGA GAA ATG GAA AAT GCG GTA GCT TTA    2496
 I   V   K   E   I   V   K   R   E   M   E   N   A   V   A   L     832

AAA GTA CCT TTG GTA GTT GAA GTG AAA GAA GGA CTG AAC TGG TAT GAG    2544
 K   V   P   L   V   V   E   V   K   E   G   L   N   W   Y   E     848

ACA AAA TAG                                                        2553
 T   K                                                              850
```

*Fig. 4 continued*

THERMOSTABLE DNA POLYMERASE FROM ANAEROCELLUM THERMOPHILUM

The present invention relates to a thermostable enzyme which is a DNA polymerase obtainable from *Anaerocellum thermophilum*.

Heat stable DNA polymerases (EC 2.7.7.7. DNA nucleotidyltransferase, DNA-directed) have been isolated from numerous thermophilic organisms (for example: Kaledin et al., 1980, *Biokimiya* Vol. 45, p. 644–651; Kaledin et al., 1981, *Biokimiya* Vol. 46, p. 1247–1254; Kaledin et al.,1982, *Biokimiya* Vol. 47, p. 1515–1521; Ruttimann, et al., 1985, *Eur. J. Biochem.* Vol. 149, p. 41–46; Neuner et al., 1990, *Arch. Microbiol.* Vol. 153, p. 205–207.)

For some organisms, the polymerase gene has been cloned and expressed (Lawyer et al., 1989, *J. Biol. Chem.* Vol. 264, p. 6427–6437; Engelke et al., 1990, *Anal. Biochem.* Vol. 191, p. 396–400; Lundberg et al., 1991, *Gene*, Vol. 108, p. 1–6; Kaledin et al., 1980 *Biokimiya* Vol. 44, p. 644–651; Kaledin et al., 1981, *Biokimiya Vol.* 46, p. 1247–1254; Kaledin et al., 1982, *Biokimiya* Vol. 47, p. 1515–1521; Ruttimann, et al., 1985, *Eur. J. Biochem.* Vol. 149, p. 41–46; Neuner et al., 1990, *Arch. Microbiol.* Vol. 153, p. 205–207; Perler et al., 1992, *Proc. Natl. Acad. Sci. USA* Vol. 89, p. 5577).

Thermophilic DNA polymerases are increasingly becoming important tools for use in molecular biology and there is growing interest in finding new polymerases which have more suitable properties and activities for use in diagnostic detection of RNA and DNA, gene cloning and DNA sequencing. At present, the thermophilic DNA polymerases mostly used for these purposes are from Thermus species like Taq polymerase from *T. aquaticus* (Brock et al 1969, *J. Bacteriol. Vol.* 98, p. 289–297).

Reverse transcription is commonly performed with viral reverse transcriptases like the enzymes isolated from *Avian myeloblastosis* virus or *Moloney murine leukemia* virus, which are active in the presence of Magnesium ions but have the disadvantages to possess RNase H-activity, which destroys the template RNA during the reverse transcription reaction and have a temperature optimum at 42° C. or 37° C., respectively.

Alternative methods are described using the reverse transcriptase activity of DNA polymerases of thermophilic organisms which are active at higher temperatures. Reverse transcription at higher temperatures is of advantage to overcome secondary structures of the RNA template which could result in premature termination of products. Thermostable DNA polymerases with reverse transcriptase activities are commonly isolated from Thermus species. These DNA polymerases however, show reverse transcriptase activity only in the presence of Manganese ions. These reaction conditions are suboptimal, because the presence of Manganese ions lowers the fidelity of the DNA polymerase transcribing the template RNA.

Therefore, it is desirable to develop a reverse transcriptase which acts at higher temperatures to overcome secondary structures of the template and is active in the presence of Magnesium ions in order to prepare cDNA from RNA templates with higher fidelity.

The present invention addresses these needs and provides a purified DNA polymerase enzyme (EC 2.7.7.7.) active at higher temperatures which has reverse transcriptase activity in the presence of magnesium ions. The invention comprises a DNA polymerase isolated from *Anaerocellum thermophilum* DSM 8995, deposited on the Deutsche Samnulung von Mikro-organismen und Zellkulturen GmbH, Mascheroder Weg 1b, D-38124 Braunschweig. In a further aspect the invention comprises a DNA polymerase that catalyses the template directed polymerisation of DNA and posess 5'-3'-polymerase activity, 5'-3'-exonuclease activity and no substantial 3'-5'-exonuclease activity.

The polymerase according to the present invention retains at least 90% of its activity after incubation for 30 Minutes at 80° C. in absence of stablilizing detergents.

In a further aspect the invention comprises a DNA polymerase having a molecular mass of about 96 to 100 kDa as determined by in situ activity PAGE analysis.

In a futther aspect the invention comprises a DNA a polymerase having reverse transcriptase activity in the presence of magnesiums ions and in the substantial absence of maganese ions. The polymerase according to the present invention exhibits a $Mg^{2+}$ dependent reverse transcriptase activity of more than 30% relative to the DNA polymerase activity which is set to 100%. In further aspect the present invention comprises a thermostable DAN polymerase wherein said polymerase exhibits a reverse transcriptaqse activity which is $Mn^{2+}$ dependent. The $Mn^{2+}$ dependent reverse transcriptase activity is more than 60% relative to the DNA polymerase activity.

In further aspect the invention comprises a thermostable reverse transcriptase. The thermostable reverse transcriptase retains more than 80% after incubation for 60 minutes at 80° C.

Moreover, DNA encoding the 96.000–100.000 daltons thermostable DNA polymerase obtainable from *Anearocellum thermophilum* has been isolated and which allows to obtain the thermostable enzyme of the present invention by expression in *E. coli*. the entire *Anearocellum thermophilum* DNA polymerase coding sequence is depicted below as SEQ ID NO. 7. The recombinant *Anaerocellum thermophilum* DNA polymerase also possesses 5'-3'polymerase activity, no substantial 3'-5'-exonuclease activity, 5'-3'-exonuclease activity and a reverse transcriptase activity which is a $Mg^{2+}$ dependent.

*Anaerocullum thermophilum* was isolated from a hot spring in the Valley of Geyser in Kamchatka (V. svetlichny et al. Mikrobilogiya, Vol. 59, No. 5 p. 871–879, 1990). *Anaerocullum thermophilum* was deposited with the Deutsche Sammlung von Mikroorganismen und Zellkulturen GmbH, Mascheroder Weg 1b, D-38124 Braunschweig under the terms of the Budapest Treaty and received DSM Accession Number 8995. The thermostable polymerase isolated from *Anaerocellum thermophilum* has a molecular weight of 96 to 100 kDa and retains more than 90% of activity after heating to 80° C. for 30 minutes in absence of stabilizing detergents. The thermostable enzyme possesses a 5'-3' polymerase activity and a reverse transcriptase activity which is $Mn^{++}$ as well as $Mg^{++}$-dependent. The thermostable enzyme may be native or recombinant and may be used for first and second strand cDNA synthesis, in cDNA cloning, DNA sequencing, DNA labeling and DNA amplification.

The present invention provides improved methods for the replication and amplification of deoxyribonucleic (DNA) and ribonucleic acid (RNA) sequences. These improvements are achieved by the discovery and application of previously unknown properties of thermoactive DNA polymerases. In a preferred embodiment, the invention provides a method for synthesizing a complementary DNA copy from an RNA template with a thermoreactive DNA polymerase. In another aspect, the invention provides methods for amplifying a DNA segment from an RNA or DNA template using a thermostable DNA polymerase (RT-PCR or PCR).

The term "reverse transcriptase" describes a class of polymerases characterized as RNA-dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation.

For recovering the native protein *Anaerocellum thermophilum* may be grown using any suitable technique, such as the technique described by Svetlichny et al., 1991, *System. Appl. Microbiol.* Vol. 14, p. 205–208. After cell growth one preferred method for isolation and purification of the enzyme is accomplished using the multi-step process as follows:

The cells are thawed, suspended in buffer A (40 mM Tris-HCl, pH 7.5, 0.1 mM EDTA, 7 mM 2-mercaptoethanol, 0.4 M NaCl, 10 mM Pefabloc™ SC (4-(2-Aminoethyl)-benzolsulfonyl-fluorid, Hydrochlorid) and lysed by twofold passage through a Gaulin homogenizer. The raw extract is cleared by centrifugation, the supernatant dialyzed against buffer B (40 mM Tris-HCl, pH 7.5, 0.1 mM EDTA, 7 mM 2-mercaptoethanol, 10% Glycerol) and applied onto a column filled with Heparin-Sepharose (Pharmacia). In each case the columns are equilibrated with the starting solvent and after application of the sample the columns are washed with the threefold of their volume with this solvent. Eluation of the first column is performed with a linear gradient of 0 to 0.5 M NaCl in Buffer B. The fractions showing polymerase activity are pooled and ammonium sulfate is added to a final concentration of 20%. This solution is applied to a hydrophobic column containing Butyl-TSK-Toyopearl (TosoHaas). This column is eluted with a falling gradient of 20 to 0% ammonium sulfate. The pool containing the activity is dialyzed and again transferred to a column of DEAE-Sepharose (Pharmacia) and eluted with a linear gradient of 0–0.5 M NaCl in buffer B. The fourth column contains Tris-Acryl-Blue (Biosepra) and is eluted as in the preceding case. Finally the active fractions are dialyzed against buffer C (20 mM Tris-HCl, pH 7.5, 0.1 mM EDTA, 7.0 mM 2-mercaptoethanol, 100 mM NaCl, 50% Glycerol).

DNA polymerase activity was either measured by incorporation of $^{32}$P-dCTP or by incorporation of digoxigenin labeled dUTP into the synthesized DNA. Detection and quantification of the incorporated digoxigenin was performed essentially as described in Holtke, H.-J.; Sagner, G. Kessler, C. and Schmitz, G., 1992, *Biotechniques* Vol. 12, p. 104 –113.

Reverse transcriptase activity was measured using oligo dT primed poly A template by incorporation of either $^{32}$P-dTTP or digoxigenin-labeled dUTP into the complementary strand. Detection of the incorporated digoxigenin was performed in analogy to the procedure used for detection of DNA polymerase activity.

In situ PAGE analysis of polymerase activity and reverse transcriptase activity was performed essentially according to the method described by Spauos A. and Hübscher U., 1983, *Methods in Enzymology* Vol. 91 p. 263–277. Some minor, but essential modifications to the original method are, that the renaturation of the SDS-denatured polypeptides is performed in the presence of magnesium ions (3 mM) and dATP (0.5–1 µM) to assist refolding.

The thermostable enzyme of this invention may also be produced by recombinant DNA techniques, as the gene encoding this enzyme has been cloned from *Anaerocellum thermophilum* genomic DNA. In a firer aspect the invention includes a recombinant plasmid comprising the vector pASK75 carrying the *Anaerocellum thermophilum* DNA polymerase gene and designated pAR10.

The isolation of the recombinant clone expressing DNA polymerase from *Anaerocellum thermophilum* includes the following steps: chromosomal DNA from *Anaerocellum thermophilum* is isolated by treating the cells with detergent e.g. SDS and a proteinase e.g. Proteinase K. The solution is extracted with phenol and chloroform and the DNA purified by precipitation with ethanol. The DNA is dissolved in Tris/EDTA buffer and the gene encoding the DNA polymerase is specifically amplified by the PCR technique using two mixed oligonucleotides (primer 1 and 2). These oligonucleotides, described in SEQ ID NO.: 1 and SPQ ID NO.: 2, were designed on the basis of conserved regions of family A DNA polymerases as published by Braithwaite D. K. and Ito J., 1993, *Nucl. Acids Res.* Vol. 21, p. 787–802. The specifically amplified fragment is ligated into an vector, preferably the pCR™II vector (Invitrogen) and the sequence is determined by cycle-sequencing. Complete isolation of the coding region and the flanking sequences of the DNA polymerase gene can be performed by restriction fragmentation of the *Anaerocellum thermophilum* DNA with another restriction enzyme as in the first round of screening and by inverse PCR (Innis et al., (1990) PCR *Protocols*; Academic Press, Inc., p. 219–227). This can be accomplished with synthesized oligonucleotide primers binding at the outer DNA sequences of the gene part but in opposite orientation. These oligonucleotides, described by SEQ ID Nos. 3 and 4, were designed on the basis of the sequences which were determined by the first above described PCR. As template *Anaerocellum thermophilum* DNA is used which is cleaved by restriction digestion and circularized by contacting with T4 DNA ligase. To isolate the coding region of the whole polymerase gene, another PCR is performed using primers as shown in SEQ ID Nos. 5 and 6 to amplify the complete DNA polymerase gene directly from genomic DNA and introducing ends compatible with the linearized expression vector.

SEQ ID NO. 1:
Primer 1: 5'-WSN GAY AAY ATH CCN GGN GT-3'
SEQ ID NO. 2:
Primer 2: 5'-NCC NAC YTC NAC YTC NAR NGG-3'
SEQ ID NO. 3:
Primer 3: 5'-CAA TTC AGG GCA GTG CTG CTG ATA TC-3'
SEQ ID NO. 4:
Primer 4: 5'-GAG CTT CTG GGC ACT CTT TTC GCC-3'
SEQ ID NO. 5:
Primer 5: 5'-CGA ATT CGG CCG TCA TGA AAC TGG TTA TAT TCG ATG GAA ACA G-3'
SEQ ID NO. 6:
Primer 6: 5'-CGA ATT GGA TCC GTT TTG TCT CAT ACC AGT TCA GTC CTT C-3'

The gene is operably linked to appropriate control sequences for expression in either prokaryotic or eucaryotic host/vector systems. The vector preferably encodes all functions required for transformation and maintenance in a suitable host, and may encode selectable markers and/or control sequences for polymerase expression. Active recombinant thermostable polymerase can be produced by transformed host cultures either continuously or after induction of expression. Active thermostable polymerase can be recovered either from host cells or from the culture media if the protein is secreted through the cell membrane.

It is also preferable that *Anaerocellum thermophilum* thermostable polymerase expression is tightly controlled in *E.coli* during cloning and expression. Vectors useful in practicing the present invention should provide varying degrees of controlled expression of *Anaerocellum thermophilum* polymerase by providing some or all of the following control features: (1) promoters or sites of initiation of transcription, either directly adjacent to the start of the polymerase gene or as fusion proteins, (2) operators which could be used to turn gene expression on or off, (3) ribosome binding sites for improved translation, and (4) transcription or translation termination sites for improved stability. Appropriate vectors used in cloning and expression of *Anaerocellum thermophilum* polymerase include, for example, phage and plasmids. Example of phage include lambda gt11 (Promega), lambda Dash (Stratagene) lambda ZapII (Stratagene). Examples of plasmids include pBR322, pBTac2 (Boehringer Mannheim), pBluescript (Stratagene), pET3A (Rosenberg, A. H. et al., (1987) *Gene* 56:125–135), pASK75 (Biometra) and pET11C (Studier, F. W. et al. (1990) *Methods in Enzymology,* 185:60–89). According to the present invention the use of a plasmid has shown to be advantageously, particularly pASK75 (Biometra). The Plasmid pASK75 carrying the *Anaerocellum thermophilum* DNA polymerase gene is then designated pAR10.

Standard protocols exist for transformation, phage infection and cell culture (Maniatis, et al. (1982) *Molecular Cloning: A Laboratory Manual*, Cold Spring Harbour Laboratory Press). Of the numerous *E. coli* strains which can be used for plasmid transformation, the preferred strains include JM110 (ATCC 47013), LE392 pUBS 520 (Maniatis et al. supra; Brinkmann et al., (1989) *Gene* 85:109–114;), JM101 (ATCC No. 33876), XL1 (Stratagene), and RR1 (ATCC no. 31343), and BL21 (DE3) plysS (Studier, F. W. et al., (1990) *Methods in Enzymology*, supra). According to the present invention the use of the *E. coli* strain LE392 pUBS 520 has shown to be advantageously. The *E. coli* strain7221 LE392 pUBS 520 transformed with the plasmid pASK75 carrying the *Anaerocellum thermophilum* DNA polymerase gene (designated pAR10) is then designated *E.coli* AR220 (DSM No. 11177). *E.coli* strain XL1. Blue (Stratagene) is among the strains that can be used for lambda phage, and Y1089 can be used for lambda gt11 lysogeny. The transformed cells are preferably grown at 37° C. and expression of the cloned gene is induced with anhydrotetracycline.

Isolation of the recombinant DNA polymerase can be performed by standard techniques. Separation and purification of the DNA polymerase from the *E.coli* extract can be performed by standard methods. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electric charge such as ion-exchange column chromatography, methods utilizing specific interaction such as affinity chromatography, methods utilizing a difference in hydrophobicity such as reversed-phase high performance liquid chromatography and methods utilizing a difference in isoelectric point such as isoelectric focussing electrophoresis.

The thermostable enzyme of this invention may be used for any purpose in which such enzyme activity is necessary or desired. In a particularly preferred embodiment, the enzyme catalyzes the nucleic acid amplification reaction known as PCR. This process for amplifying nucleic acid sequences is disclosed and claimed in EP 0 201 189. The PCR nucleic acid amplification method involves amplifying at least one specific nucleic acid sequence contained in a nucleic acid or a mixture of nucleic acids and produces double stranded DNA. Any nucleic acid sequence, in purified or nonpurified form, can be utilized as the starting nucleic acid(s), provided it contains or is suspected to contain the specific nucleic acid sequence desired. The nucleic acid to be amplified can be obtained from any source, for example, from plasmids such as pBR322, from cloned DNA or RNA, from natural DNA or RNA from any source, including bacteria, yeast, viruses, organelles, and higher organisms such as plants and animals, or from preparations of nucleic acids made in vitro. DNA or RNA may be extracted from blood, tissue material such as chorionic villi, or amniotic cells by a variety of techniques. See, e.g., Maniatis T. et al., 1982, *Molecular Cloning: A Laboratory Manual* (Cold Spring Harbor Laboratory, Cold Spring Harbor, N.Y.) pp. 280–281. Thus the process may employ, for example, DNA or RNA, including messenger RNA, which DNA or RNA may be single-stranded or double-stranded. In addition, a DNA-RNA hybrid which contains one strand of each may be utilized.

The amplification of target sequences in DNA or from RNA may be performed to proof the presence of a particular sequence in the sample of nucleic acid to be analyzed or to clone a specific gene. DNA polymerase from *Anaerocellum thermophilum* is very useful for these processes. Due to the fact that the DNA polymerase from *Anaerocellum thermophilum* requires $Mg^{++}$ ions as a cofactor instead of $Mn^{++}$ like the other DNA polymerases from thermophilic organisms with reverse transcriptase activity of the state of the art the RNA templates can be copied with higher fidelity. These properties make DNA polymerase from *Anaerocellum thermophilum* a very useful tool for the molecular biologist. DNA polymerase from *Anaerocellum thermophilum* may also be used to simplify and improve methods for detection of RNA target molecules in a sample. In these methods DNA polymerase from *Anaerocellum thermophilum* catalyzes: (a) reverse transcription, (b) second strand cDNA synthesis, and, if desired, (c) amplification by PCR. The use of DNA polymerase from *Anaerocellum thermophilum* in the described methods eliminates the previous requirement of two sets of incubation conditions which were necessary due to the use of different enzymes for each step. The use of DNA polymerase from *Anaerocellum thermophilum* provides RNA reverse transcription and amplification of the resulting complementary DNA with enhanced specificity and with fewer steps than previous RNA cloning and diagnostic methods.

As control proteins DNA polymerase I and Klenow fragment of *E.coli* and DNA polymerase from *Thermus thermophilus* were analyzed on the same gel. Using these proteins as standards the apparent molecular weight of DNA polymerase from *Anaerocellum thermophilum* of 96.000 to 100.000 Daltons can be deduced.

FIG. 2 shows results obtained from assays determining the relative activity of the reverse transcriptase in dependence of varying concentrations of magnesium and manganese ions.

Figure 1:
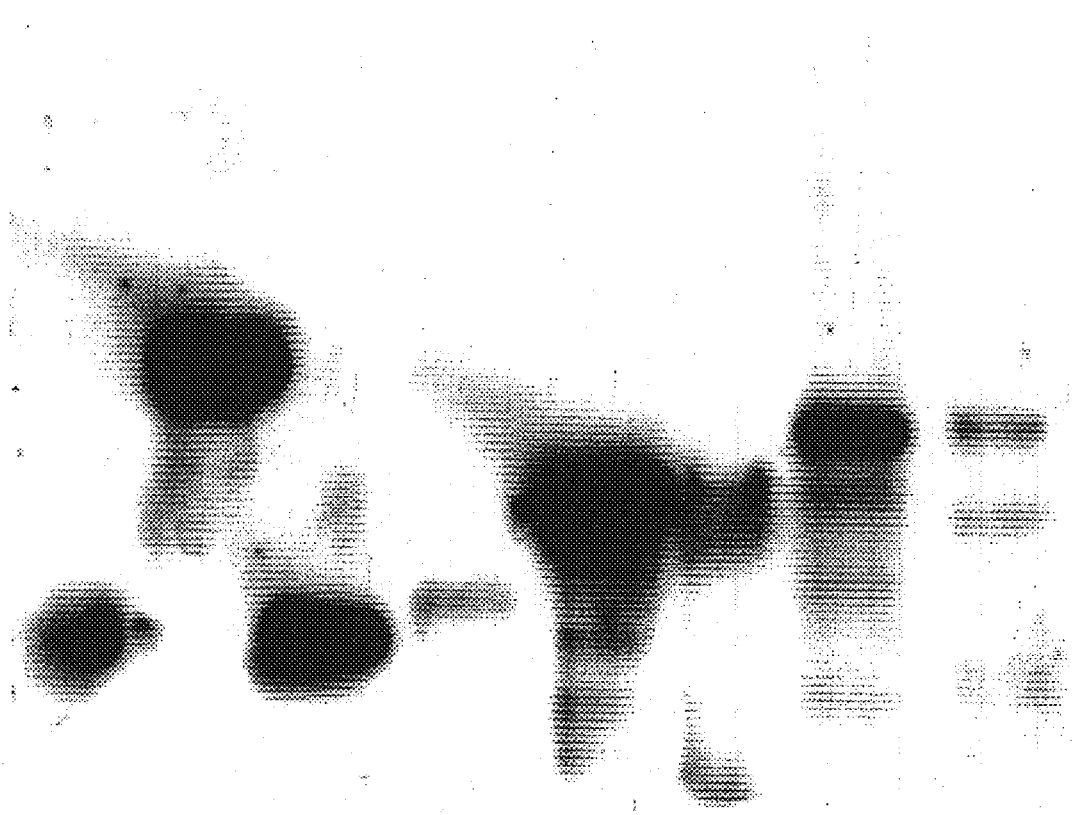
FIG. 1 shows a photograph of a DNA polymerase assay performed in situ. The DNA polymerase activity of DNA polymerase from *Anaerocellum thermophilum* is analysed in comparison with DNA polymerase I and Klenow fragment of *E. coli* and DNA polymerase from *Thermus thermophilus*. A fraction of DNA polymerase from *Anaerocellum thermophilum* was submitted to electrophoresis on a SDS-polyacrylamide gel containing activated (DNAseI treated) DNA. After electrophoresis the SDS was removed, the proteins were renatured over night and incubated at 72° C. in the presence of magnesium salt, dNTPs and digoxigenin labeled dUTPs to allow synthesis of the complementary strand. The nucleic acid was blotted to a nylon membrane and the newly synthesized DNA detected by a chemiluminescence reaction.
Figure 3:
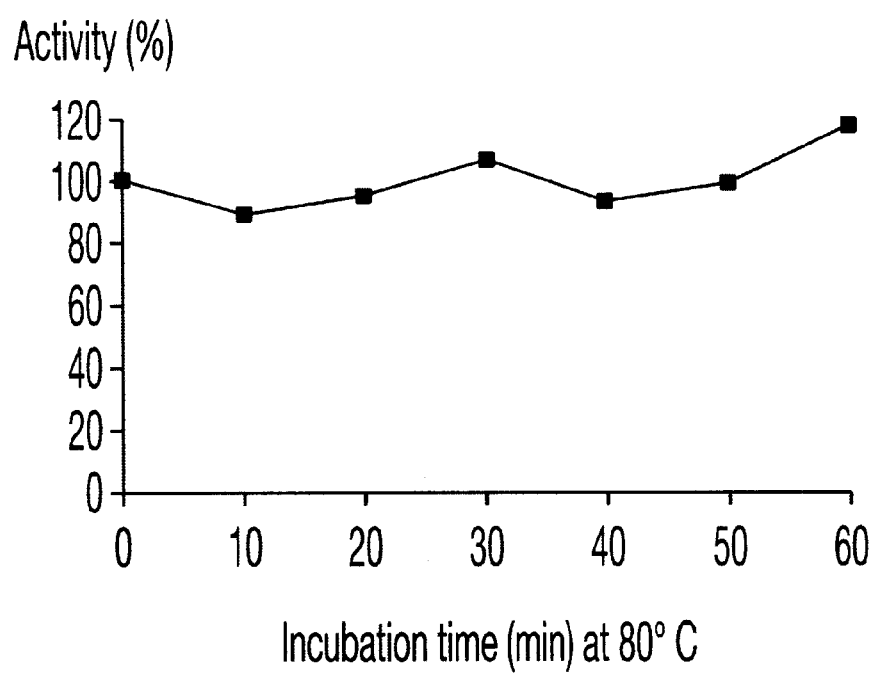

FIG. 3 shows the thermostability of DNA polymerase from *Anaerocellum thermophilum*. Aliquots of the DNA polymerase were incubated at 80° C. and the activity measured at the times indicated in the figure.

FIG. 4 shows the DNA sequence (SEQ ID NO: 7) of the polymerase gene of *Anaerocellum thermophilum* and the derived peptide sequence (SEQ ID NO: 8) for *Anaerocellum thermophilum*.

Figure 5:
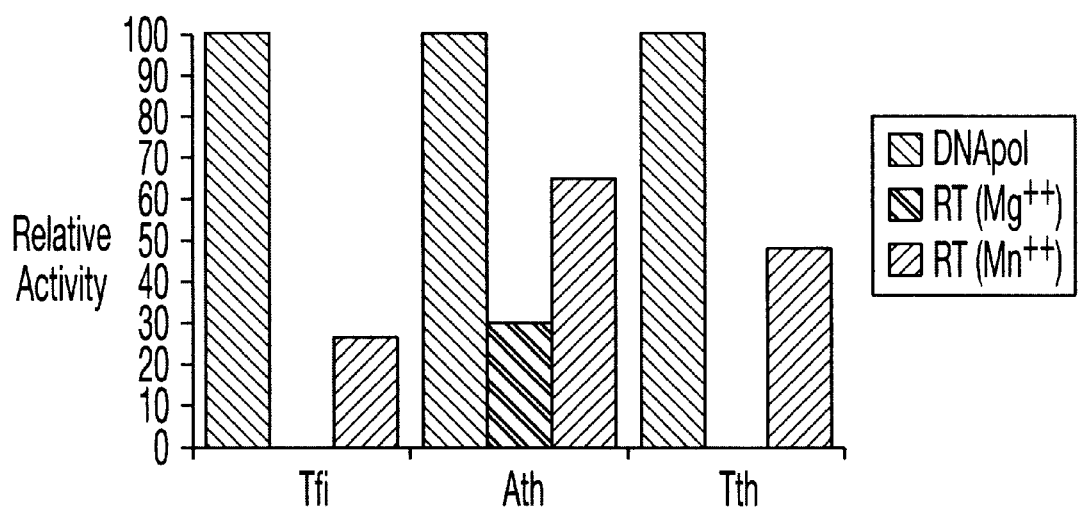

FIG. 5 shows the comparison ot the reverse transcriptase activity of *Anaerocellum thermophilum* polymerase with *Thermus filiformis* and *Thermus thermophilus*.

EXAMPLE 1

Isolation of DNA Polymerase

For recovering the native protein *Anaerocellum thermophilum* may be grown using any suitable technique, such as the technique described by Svetlichny et al., 1991, *System. Appl. Microbiol.* Vol. 14, p. 205–208. After cell growth one preferred method for isolation and purification of the enzyme is accomplished using the multi-step process as follows:

The cells are thawed, suspended in buffer A (40 mM Tris-HCl, pH 7.5, 0.1 mM EDTA, 7 mM 2-mercaptoethanol, 0.4 M NaCl, 10 mM Pefabloc™ SC (4-(2-Aminoethyl)-benzolsulfonyl-fluorid, Hydrochlorid) and lysed by twofold passage through a Gaulin homogenizer. The raw extract is cleared by centrifgation, the supernatant dialyzed against buffer B (40 mM Tris-HCl, pH 7.5, 0.1 mM EDTA, 7 mM 2-mercaptoethanol, 10% Glycerol) and applied onto a column filled with Heparin-Sepharose (Pharmacia). In each case the columns are equilibrated with the starting solvent and after application of the sample the columns are washed with the threefold of their volume with this solvent. Eluation of the first column is performed with a linear gradient of 0 to 0.5 M NaCl in Buffer B. The fractions showing polymerase activity are pooled and ammonium sulfate is added to a final concentration of 20%. This solution is applied to a hydrophobic column containing Butyl-TSK-Toyopearl (TosoHaas). This column is eluted with a falling gradient of 20 to 0% ammonium sulfate. The pool containing the activity is dialyzed and again transferred to a column of DEAE-Sepharose (Pharmacia) and eluted with a linear gradient of 0–0.5 M NaCl in buffer B. The fourth column contains Tris-Acryl-Blue (Biosepra) and is eluted as in the preceding case. Finally the active fractions are dialyzed against buffer C (20 mM Tris-HCl, pH 7.5, 0.1 mM EDTA, 7.0 mM 2-mercaptoethanol, 100 mM NaCl, 50% Glycerol).

EXAMPLE 2

Detection of Endonuclease, Exonuclease and Ribonuclease Activities

Absence of endonuclease activity: 1 μg of plasmid DNA is incubated for 4 hours with an excess of purified DNA polymerase in 50 μl of test buffer with a paraffin oil overlay at 72° C.

Absence of nonspecific exonuclease activity: 1 μg of EcoRI/HindIII-fragments of lambda DNA are incubated in 50 μl of test buffer in the absence and presence of dNTPs (1 mM final concentration each) with an excess of purified DNA polymerase for 4 hours at 72° C. with a paraffin overlay.

Absence of ribonuclease activity: 3 μg of MS2 RNA are incubated with an excess of DNA polymerase in 20 μl of test buffer for 4 hours at 72° C. The RNA is subsequently analyzed by electrophoresis in a MOPS gel (Maniatis et al., 1982, *Molecular Cloning: A Laboratory Manual*, Cold Spring Harbor, N.Y.).

EXAMPLE 3

Determination of DNA Polymerase Activity

DNA polymerase activity was either measured by incorporation of $^{32}$P-dCTP or by incorporation of digoxigenin labeled dUTP into the synthesized DNA.

Detection and quantification of $^{32}$P-dCTP incorporation was measured as follows: The reaction mixture contained 50 mM Tris-HCl, pH 8.5; 12.5 mM $(NH_4)_2SO_4$; 10 mM KCl; 5 mM $MgCl_2$; 10 mM 2-mercaptoethanol, 200 μg/ml BSA, 200 μM of dATP, dGTP and dTTP, 100 μM dCTP, 12 μg of DNAse activated DNA from calf thymus and 0.1 μl of $^{32}$P-dCTP (10 mCi/ml, 3000 Ci/mmol). After incubation for 30 min. at 70° C. the samples were placed on ice, 250 μl of 10% trichloroacetic acid were added, the samples mixed and incubated for 10 more min. on ice. 150 μl of the samples were filtrated through nylon membranes, the filters washed four times with 5% trichloroacetic acid. The filters were dried for 30 minutes at 80° C. and the radioactivity bound to the filters determined in a Packard Matrix 96 Direct Beta Counter.

Detection and quantification of the incorporated digoxigenin was performed essentially as described in Höltke, H.-J.; Sagner, G; Kessler, C. and Schmitz, G., 1992, *Biotechniques* Vol. 12, p. 104 –113. Typically, this assay is performed in a total volume of 50 μl of a reaction mixture composed of 1 or 2 μl of diluted (0.05 U–0.01 U) DNA polymerase and 50 mM Tris-HCl, pH 8.5; 12.5 mM $(NH_4)_2SO_4$; 10 mM KCl; 5 mM $MgCl_2$; 10 mM 2-mercaptoethanol; 33 μM dNTPs; 200 μg/ml BSA; 12 μg of DNAse activated DNA from calf thymus and 0.036 μM digoxigenin-dUTP.

The samples are incubated for 30 min. at 72° C., the reaction is stopped by addition of 2 μl 0.5 M EDTA and the tubes placed on ice. After addition of 8 μl 5 M NaCl and 150 μl of Ethanol (precooled to −20° C.) the DNA is precipitated by incubation for 15 min. on ice and pelleted by centrifugation for 10 min. at 13000xrpm and 4° C. The pellet is washed with 100 μl of 70% Ethanol (precooled to −20° C.) and 0.2 M NaCl, centrifuged again and dried under vacuum. The pellets are dissolved in 50 μl Tris-EDTA (10 mM/0.1 mM; pH 7.5). 5 μl of the sample are spotted into a well of a nylon membrane bottomed white microwell plate (Pall Filtrationstechnik GmbH, Dreieich, FRG, product no: SM045BWP). The DNA is fixed to the membrane by baking for 10 min. at 70° C. The DNA loaded wells are filled with 100 μl of 0.45 μm-filtrated 1% blocking solution (100 mM maleic acid, 150 mM NaCl, 1% (w/v) casein, pH 7.5). All following incubation steps are done at room temperature. After incubation for 2 min. the solution is sucked through the membrane with a suitable vacuum manifold at −0.4 bar. After repeating the washing step, the wells are filled with 100 μl of a 1:10000-dilution anti-digoxigenin-AP, Fab fragments (Boehringer Mannheim, FRG, no: 1093274) diluted in the blocking solution described above. After incubation for 2 min. and sucking this step is repeated once. The wells are washed twice under vacuum with 200 μl of washing buffer 1 (100 mM maleic acid, 150 mM NaCl, 0.3%(v/v) Tween™ 20, pH 7.5). After washing another two times under vacuum with 200 μl washing buffer 2 (10 mM Tris-HCl, 100 mM NaCl, 50 mM $MgCl_2$, pH 9.5), 50 μl of CSPD™ (Boehringer Mannheim, no: 1655884) diluted 1:100 in washing buffer 2, which serves as a chemiluminescent substrate for the alkaline phosphatase, are added to the wells and the microwell plate is incubated for 5 min. at room temperature. The solution is then sucked through the membrane and after 10 min. fierier incubation at room temperature the RLU/s (Relative Light Unit per second) are detected in a Luminometer e.g. MicroLumat LB 96 P (EG&G Berthold, Wildbad, FRG).

With a serial dilution of Taq DNA polymerase a standard curve is prepared from which the linear range serves as a standard for the activity determination of the DNA polymerase to be analyzed.

EXAMPLE 4

Determination of Reverse Transcriptase Activity

Reverse transcriptase activity was measured using oligo dT primed poly A template by incorporation of either $^{32}$P-dTTP or digoxigenin-labeled dUTP into the complementary strand. Incorporation of $^{32}$P-dTTP was measured in a mixture containing 1 µg of poly A.(dT)$_{15}$, 500 µM of dTTP, 100 mg/ml BSA, 10 mM Tris-HCl, pH 8.5, 20 mM KCl, 0.5–10 mM MgCl$_2$ or 0.1–5 mM MnCl$_2$, 10 mM DTE, 0.5 µl of $^{32}$P-dTTP (10 mM Ci/ml, 3000 Ci/mmol) and various amounts of DNA polymerase. The incubation temperature used was 50° C. The incorporated radioactivity was determined as described in the assay for determination of DNA polymerase activity.

Incorporation of digoxigenin-dUTP was measured in a mixture containing 1 µg of poly A.(dT)$_{15}$, 330 µM of dTTP, 0.36 µM of digoxigenin-dUTP, 200 mg/ml BSA, 10 mM Tris-HCl, pH 8.5, 20 mM KCl, 0.5–10 mM MgCl$_2$ or 0.1–5 mM MnCl$_2$, 10 mM DTE and various amounts of DNA polymerase. The incubation temperature used was 50° C. Detection of the radioactivity incorporated was performed in analogy to the procedure used for detection of DNA polymerase activity.

EXAMPLE 5

Detection of DNA Polymerase and Reverse Transcriptase Activity in situ

In situ PAGE analysis of polymerase activity and reverse transcriptase activity was performed essentially according to the method described by Spanos A. and Hübscher U., 1983, *Methods in Enzymology* Vol. 91 p. 263–277. Some minor, but essential modifications to the original method are, that the renaturation of the SDS-denatured polypeptides is performed in the presence of magnesium ions (3 mM) and DATP (0.5–1 µM) to assist refolding. In brief the method is as follows:

After separation of polypeptides from either crude cell extracts or purified samples on a denaturing 8% polyacrylamide gel (stacking gel 5% acrylamide) which contains 150 µg activated calf thymus DNA per ml gel volume, the gel is washed four times (15–30 min. each at room temperature with moderate shaking) in excess renaturation buffer (Tris-HCl, 50 mM, pH 8.4; EDTA, 1 mM; 2-mercaptoethanol, 3 mM; KCl, 50 mM; Glycerol, 5–10%) to remove SDS. Then the gel is incubated overnight in the same buffer, including 3 mM MgCl$_2$ and 0.5–1 µM DATP at 4° C. without agitation. The first four washes are repeated the next day with renaturation buffer. After the removal of SDS and renaturation of the proteins the gel is transferred into the reaction mixture consisting of Tris-HCl, 50 mM, pH 8.4; KCl, 50 mM, DTT, 3 mM; MgCl$_2$, 7 mM; 12 µM of DATP, dCTP, dGTP (each), 8 µM dTTP and 4 µM Dig-dUTP; 10% (v/v) glycerol. The gel is first incubated under shaking at room temperature (30 min.) and then slowly warmed up to 72° C. by temperature increments of 5° C. At each temperature interval DNA synthesis is allowed to proceed for 30 min., in order to detect also polymerase activity of mesophile control polymerases. After DNA synthesis, the DNA is transferred either electrophoretically (0.25×TBE) or by capillary blotting (15×SSC) to nylon membranes (Boehringer Mannheim) and UV crosslinked. Newly synthesized Dig-labeled DNA is detected according to the procedure described for analysis of DNA polymerase activity.

EXAMPLE 6

Cloning of the *Anaerocellum thermophilum* DNA Polymerase Gene

Preparation of chromosomal DNA from *Anaerocellum thermophilum*

0.8 g biomass of *Anaerocellum thermophilum* was suspended in 20 ml 1M KCl and centrifuged. Then the pellet was resuspended in 4.8 ml SET-buffer (150 mM NaCl, 15 mM EDTA, pH 8.0, 60 mM Tris-HCl, pH 8.0, 50 µg/µl RNaseA), after which 1 ml 20% SDS and 50 µl of proteinase K (10 mg/ml) were added. The mixture was kept at 37° C. for 45 min. After extraction with phenol and chloroform the DNA was precipitated with ethanol and dissolved in H$_2$O. Thus about 3.8 mg of DNA were obtained.

Amplification of specific DNA by PCR

For amplification of the gene encoding the DNA polymerase of *Anaerocellum thermophilum* by the PCR technique two mixed oligonucleotides (primer 1 and 2) were designed on the basis of conserved regions of family A DNA polymerases as published by Braithwaite D. K. and Ito J., 1993, *Nucl. Acids Res.* Vol. 21, p. 787–802.

SEQ ID NO. 1:
Primer 1: 5'-WSN GAY AAY ATH CCN GGN GT-3'
SEQ ID NO.2:
Primer 2: 5'-NCC NAC YTC NAC YTC NAR NGG-3'

The PCR amplification was performed in 100 µl buffer containing 750 ng of genomic DNA from *Anaerocellum thermophilum*, 10 mM Tris-HCl, pH 8.8, 2.5 mM MgCl$_2$, 50 mM KCl, 200 µM dNTPs, 100 pmoles of each primer and 2.5 units of Taq polymerase (Boehringer Mainheim GmbH). The target sequence was amplified by first denaturing at 95° C. for 2 min. followed by 30 cycles of 95° C. for 0.5 min, 50° C. for 1 min. and 72° C. for 2 min. Thermal cycling was performed in a Perkin Elmer GenAmp 9600 thermal cycler. Agarose gel electrophoresis showed, that a fragment of approximately 1,900 base pairs was amplified specifically. This fragment was ligated into the pCR™II vector (Invitrogen) and the sequence determined by cycle-sequencing. The amino acid sequence deduced from this nucleotide sequence was very similar to that of other known DNA polymerases, so that primer 3 and 4 could be designed for inverse PCR.

SEQ ID NO. 3:
Primer 3: 5'-CAA TTC AGG GCA GTG CTG CTG ATA TC-3'
SEQ ID NO.4:
Primer 4: 5'-GAG CTT CTG GGC ACT CTT TTC GCC-3'

Inverse PCR was performed essentially as described in Triglia T. et al., 1988, Nucleic Acids Research Vol. 16, p. 8186.5 µg genomic DNA from *Anaerocellum thermophilum* were cleaved by EcoRI according to supplier's specifications (Boehringer Mannheim GmbH) and treated with an equal volume of phenol/chloroform mixture. The aqueous phase was removed, the DNA precipitated with ethanol and collected by centrifuigation.

For circularization the digested DNA was diluted to a concentration of 50 ng/µl in ligation buffer (Boehringer Mannheim GmbH). The ligation reaction was initiated by the addition of T4 DNA Ligase (Boehringer Mannheim GmbH) to a concentration of 0.2 units/µl and the reaction was allowed to proceed for 15 hrs at 15° C. The ligated DNA was then precipitated with ethanol and collected by centrifugation.

The PCR was performed in 50 µl buffer containing 50 mM Tris-Cl, pH 9.2, 16 mM $(NH_4)_2SO_4$, 2.25 mM $MgCl_2$, 2% (v/v) DMSO, 0.1% (v/v) Tween™ 20 $(Poly(oxyethylen)_n$-sorbitan-mono-laurat), 700 ng of circularized DNA obtained as described above, 50 pmoles of each primer, 500 µM dNTP and 0.75 µl enzyme mix (Expand Long Template PCR System, Boehringer Mannheim GmbH).

The cycle conditions were as follows:

| | |
|---|---|
| 1x | denaturation of template for 2 min. at 92° C. |
| 10x | denaturation at 92° C. for 10 sec. |
| | annealing at 64° C. for 30 |
| | elongation at 68° C. for 2 min. |
| 20x | denaturation at 92° C. for 10 sec. |
| | annealing at 64° C. for 30 sec. |
| | elongation at 68° C. for 2 min. |
| | + cycle elongation of 20 sec. for each cycle |

Agarose gel electrophoresis revealed a specifically amplified DNA fragment 6,500 base pairs long. The DNA fragment was ligated into the pCR™II vector (Invitrogen) and sequenced. Deduced from this sequence primer 5 and 6 coding for the 5'- and 3'-ends, respectively, of the polymerase region could be designed. Primer 5 contained a EclXI site and primer 6 contained a BamHI site. The PCR was performed under the same conditions as described above (inverse PCR) using 750 ng genomic DNA from *Anaerocellum thermophilum* as template.
SEQ ID NO. 5:
Primer 5: 5'-CGA ATT CGG CCG TCA TGA AAC TGG TTA TAT TCG ATG GAA ACA G-3'
SEQ ID NO. 6:
Primer 6: 5'-CGA ATT GGA TCC GTT TTG TCT CAT ACC AGT TCA GTC CTT C-3'
Cloning and Expression The PCR product was purified by electrophoresis of 20 µl of the PCR mixture on a 0.8% agarose gel. The 2.552 kb band of the polymerase coding region was purified from the agarose by phenol extraction. The DNA was then treated with chloroform and precipitated with ethanol. The pellet was resuspended and digested with EclXI and BamHI according to supplier's specification (Boehringer Mannheim GmbH) to give cohesive ends for directional cloning. The DNA was ligated into the expression vector pASK75 (Biometra) that had also been digested with EclXI and BamHI. The ligated products were introduced into *E.coli* strain LE392 pUBS520 (Brinkmann U., et al., 1989, *Gene* Vol. 85, p. 109–114) by transformation. Transformants were grown on L-agar containing 100 µg/ml ampicillin and 50 µg/ml kanamycin to allow selection of recombinants. Colonies were picked and grown in L-broth containing 100 µg/ml ampicillin and 50 µg/ml kanamycin, and plasmid DNA was prepared by alkaline lysis. The plasmids were screened for insertions by digestion with BamHI. Those recombinants containing inserts were grown in L-broth containing ampicillin and kanamycin and tested for the expression of thermophilic DNA polymerase by induction of exponentially growing culture with 0.2 pg/ml anhydrotetracycline and assaying the heat-treated extracts for DNA polymerase activity as described above (determination of DNA polymerase activity). A recombinant expressing the DNA polymerase from *Anaerocellum thermophilum* was obtained. The strain was designated *E.coli* AR220 (DSM No. 11177) and the plasmid pAR10.

EXAMPLE 7

DNA polymerase from *Anaerocellum thermophilum* was compared with DNA polymerases from *Thermus thermophilus* and *Thermus filiformis*. Similar amounts (units) of the DNA polymerases were analyzed. Each enzyme was tested for DNA polymerase activity, for reverse transcriptase activity in the presence of Mg++ (5 mM) and reverse transcriptase activity in the presence of Mn++ (1 mM) under the reaction conditions optimal for the individual enzymes. In order to compare the ratio of DNA polymerase to reverse transcriptase activity, the relative light units (RLU) measured in the DNA polymerase assay were set to 100. The RLUs measured in the reverse transcriptase activity tests are expressed as percent of the polymerase activity. Results are shown in FIG. 5.

We claim:

1. An isolated polypeptide encoded by SEQ ID NO:7.

2. The polypeptide of claim 1 which has an apparent molecular weight between about 96,000 to about 100,000 daltons.

3. A process for the preparation of the polypeptide of claim 1 comprising the steps of:
   a. culturing a cell comprising SEQ ID NO:7; and
   b. isolating the polypeptide from the cell.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: amplification primer
<221> NAME/KEY: misc_feature
<222> LOCATION: 3,15,18
<223> OTHER INFORMATION: n= a,t,c, or g

<400> SEQUENCE: 1
wsngayaaya thccnggngt                                            20

<210> SEQ ID NO 2
<211> LENGTH: 21

```
<212> TYPE: DNA
<213> ORGANISM: Artificial Sequence
<220> FEATURE:
<223> OTHER INFORMATION: Description of Artificial Sequence:
      amplification primer
<221> NAME/KEY: misc_feature
<222> LOCATION: 1,4,10,16,19
<223> OTHER INFORMATION: n= a,t,c, or g

<400> SEQUENCE: 2
nccnacytcn acytcnarng g                                              21

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:
      amplification primer

<400> SEQUENCE: 3
caattcaggg cagtgctgct gatatc                                         26

SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      amplification primer

<400> SEQUENCE: 4
gagcttctgg gcactcttttt cgcc                                          24

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence:
      amplification primer

<400> SEQUENCE: 5
cgaattcggc cgtcatgaaa ctggttatat tcgatggaaa ca                       42

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence:
      amplification primer

<400> SEQUENCE: 6
cgaattggat ccgttttgtc tcataccagt tcagtcctcc                          40

<210> SEQ ID NO 7
<211> LENGTH: 2553
<212> TYPE: DNA
<213> ORGANISM: Anaerocellum thermophilum
<220> FEATURE:
<221> NAME/KEY: CDS
<222> LOCATION: (1)..(2553)
<223> OTHER INFORMATION:

<400> SEQUENCE: 7 atg aaa ctg gtt ata ttc gat gga aac agc att ttg tac aga gcc ttt     48
Met Lys Leu Val Ile Phe Asp Gly Asn Ser Ile Leu Tyr Arg Ala Phe
```

-continued

```
1               5                   10                  15
ttt gct ctt cct gaa ctg aca acc tca aat aat att cca aca aac gct      96
Phe Ala Leu Pro Glu Leu Thr Thr Ser Asn Asn Ile Pro Thr Asn Ala
             20                  25                  30 ata tat gga ttt gta aat gtg ata ttg aaa tat tta gaa caa gaa aaa     144
Ile Tyr Gly Phe Val Asn Val Ile Leu Lys Tyr Leu Glu Gln Glu Lys
         35                  40                  45 cct gat tat gtt gct gta gca ttt gat aaa aga gga aga gag gca cga    192
Pro Asp Tyr Val Ala Val Ala Phe Asp Lys Arg Gly Arg Glu Ala Arg
 50                  55                  60 aaa agc gag tac gaa gaa tat aaa gct aac aga aaa cct atg cca gat    240
Lys Ser Glu Tyr Glu Glu Tyr Lys Ala Asn Arg Lys Pro Met Pro Asp
 65              70                  75                  80 aac ctt caa gta caa atc cct tat gtt cga gag att ctt tat gcc ttt    288
Asn Leu Gln Val Gln Ile Pro Tyr Val Arg Glu Ile Leu Tyr Ala Phe
                 85                  90                  95 aac att cca ata att gag ttt gaa gga tat gaa gca gat gat gta atc    336
Asn Ile Pro Ile Ile Glu Phe Glu Gly Tyr Glu Ala Asp Asp Val Ile
             100                 105                 110 ggt tca ctt gtt aac cag ttc aaa aat act ggt ttg gat att gtt att    384
Gly Ser Leu Val Asn Gln Phe Lys Asn Thr Gly Leu Asp Ile Val Ile
         115                 120                 125 att acg ggt gac agg gat act ctt cag ttg ctc gac aaa aat gta gtt    432
Ile Thr Gly Asp Arg Asp Thr Leu Gln Leu Leu Asp Lys Asn Val Val
130                 135                 140 gtg aag att gtt tca aca aaa ttt gat aaa aca gta gaa gat ttg tac    480
Val Lys Ile Val Ser Thr Lys Phe Asp Lys Thr Val Glu Asp Leu Tyr
145                 150                 155                 160 act gtg gaa aat gtt aaa gaa aaa tat ggg gtt tgg gca aat caa gtg    528
Thr Val Glu Asn Val Lys Glu Lys Tyr Gly Val Trp Ala Asn Gln Val
                165                 170                 175 cct gat tac aaa gcg ctt gtt gga gac caa tca gat aac att ccc ggg    576
Pro Asp Tyr Lys Ala Leu Val Gly Asp Gln Ser Asp Asn Ile Pro Gly
            180                 185                 190 gta aag gga att ggc gaa aag agt gcc cag aag ctc ttg gaa gag tac    624
Val Lys Gly Ile Gly Glu Lys Ser Ala Gln Lys Leu Leu Glu Glu Tyr
        195                 200                 205 tca tcc tta gaa gag ata tac caa aat tta gat aaa att aaa agt tcc    672
Ser Ser Leu Glu Glu Ile Tyr Gln Asn Leu Asp Lys Ile Lys Ser Ser
    210                 215                 220 att cgt gaa aag tta gaa gca gga aaa gat atg gcg ttt tta tcc aag    720
Ile Arg Glu Lys Leu Glu Ala Gly Lys Asp Met Ala Phe Leu Ser Lys
225                 230                 235                 240 cgc tta gca aca att gta tgt gat tta cca cta aat gtt aaa ctt gaa    768
Arg Leu Ala Thr Ile Val Cys Asp Leu Pro Leu Asn Val Lys Leu Glu
                245                 250                 255 gac cta aga aca aaa gag tgg aac aag gaa agg ctc tat gag att ttg    816
Asp Leu Arg Thr Lys Glu Trp Asn Lys Glu Arg Leu Tyr Glu Ile Leu
            260                 265                 270 gtg cag tta gag ttc aaa agc ata ata aaa cgg tta gga gtt cta tca    864
Val Gln Leu Glu Phe Lys Ser Ile Ile Lys Arg Leu Gly Val Leu Ser
        275                 280                 285 gaa gtt caa ttt gaa ttt gtt cag cag cga acc gat ata cct gac gtt    912
Glu Val Gln Phe Glu Phe Val Gln Gln Arg Thr Asp Ile Pro Asp Val
    290                 295                 300 gaa caa aaa gag ctt gaa agt att tca caa ata aga tca aaa gag att    960
Glu Gln Lys Glu Leu Glu Ser Ile Ser Gln Ile Arg Ser Lys Glu Ile
305                 310                 315                 320 cca tta atg ttt gta cag ggc gaa aaa tgt ttt tat tta tat gat caa   1008
```

```
                Pro Leu Met Phe Val Gln Gly Glu Lys Cys Phe Tyr Leu Tyr Asp Gln
                                325                 330                 335 gaa agt aat act gta ttt ata aca agt aat aaa ctt ttg ata gag gag      1056
Glu Ser Asn Thr Val Phe Ile Thr Ser Asn Lys Leu Leu Ile Glu Glu
            340                 345                 350 att tta aaa agt gat act gtg aaa att atg tat gat ttg aaa aat ata      1104
Ile Leu Lys Ser Asp Thr Val Lys Ile Met Tyr Asp Leu Lys Asn Ile
            355                 360                 365 ttt cat caa ctc aac ctg gaa gac act aat aat att aaa aat tgc gaa      1152
Phe His Gln Leu Asn Leu Glu Asp Thr Asn Asn Ile Lys Asn Cys Glu
370                 375                 380 gat gta atg att gct tcc tat gtt ctt gac agc aca aga agt tca tat      1200
Asp Val Met Ile Ala Ser Tyr Val Leu Asp Ser Thr Arg Ser Ser Tyr
385                 390                 395                 400 gag tta gaa acg ttg ttt gta tct tac ttg aac act gac ata gaa gct      1248
Glu Leu Glu Thr Leu Phe Val Ser Tyr Leu Asn Thr Asp Ile Glu Ala
                405                 410                 415 gta aaa aaa gac aag aag ata gtc tct gtg gta ctt cta aaa cgg tta      1296
Val Lys Lys Asp Lys Lys Ile Val Ser Val Val Leu Leu Lys Arg Leu
            420                 425                 430 tgg gac gag ctt ttg aga tta ata gat tta aat tca tgc cag ttt tta      1344
Trp Asp Glu Leu Leu Arg Leu Ile Asp Leu Asn Ser Cys Gln Phe Leu
            435                 440                 445 tat gag aat ata gaa aga cct ctt atc cca gtt cta tat gaa atg gaa      1392
Tyr Glu Asn Ile Glu Arg Pro Leu Ile Pro Val Leu Tyr Glu Met Glu
            450                 455                 460 aaa aca gga ttt aag gtg gat aga gat gcc ctc atc caa tat acc aaa      1440
Lys Thr Gly Phe Lys Val Asp Arg Asp Ala Leu Ile Gln Tyr Thr Lys
465                 470                 475                 480 gag att gaa aac aaa ata tta aaa ctt gaa acg cag ata tac cag att      1488
Glu Ile Glu Asn Lys Ile Leu Lys Leu Glu Thr Gln Ile Tyr Gln Ile
                485                 490                 495 gca ggt gag tgg ttt aac ata aat tca ccg aaa cag ctt tct tac att      1536
Ala Gly Glu Trp Phe Asn Ile Asn Ser Pro Lys Gln Leu Ser Tyr Ile
            500                 505                 510 ttg ttt gaa aag cta aaa ctt cct gta ata aag aag aca aaa aca gga      1584
Leu Phe Glu Lys Leu Lys Leu Pro Val Ile Lys Lys Thr Lys Thr Gly
            515                 520                 525 tat tcc act gat gcc gag gtt tta gaa gag ctt ttt gac aaa cat gaa      1632
Tyr Ser Thr Asp Ala Glu Val Leu Glu Glu Leu Phe Asp Lys His Glu
            530                 535                 540 ata gtt cct ctt att ttg gat tac agg atg tat aca aag ata ctg aca      1680
Ile Val Pro Leu Ile Leu Asp Tyr Arg Met Tyr Thr Lys Ile Leu Thr
545                 550                 555                 560 act tac tgt cag gga tta cta cag gca ata aat cct tct tcg ggt aga      1728
Thr Tyr Cys Gln Gly Leu Leu Gln Ala Ile Asn Pro Ser Ser Gly Arg
                565                 570                 575 gtt cat aca acc ttt atc caa aca ggt aca gcc aca gga aga ctt gca      1776
Val His Thr Thr Phe Ile Gln Thr Gly Thr Ala Thr Gly Arg Leu Ala
            580                 585                 590 agc agc gat cct aat tta caa aat ata cct gta aaa tat gat gag ggg      1824
Ser Ser Asp Pro Asn Leu Gln Asn Ile Pro Val Lys Tyr Asp Glu Gly
            595                 600                 605 aaa ttg ata cga aag gtt ttt gta cct gag ggt gga cat gta ctg att      1872
Lys Leu Ile Arg Lys Val Phe Val Pro Glu Gly Gly His Val Leu Ile
            610                 615                 620 gat gca gat tat tcc caa att gag ctg aga ata ctt gcc cat att tct      1920
Asp Ala Asp Tyr Ser Gln Ile Glu Leu Arg Ile Leu Ala His Ile Ser
625                 630                 635                 640
```

```
gaa gat gaa aga ctt ata agt gct ttc aaa aat aat gtt gac att cat    1968
Glu Asp Glu Arg Leu Ile Ser Ala Phe Lys Asn Asn Val Asp Ile His
            645                 650                 655 tcg cag aca gca gct gag gtt ttt ggt gta gac ata gcc gat gtt act    2016
Ser Gln Thr Ala Ala Glu Val Phe Gly Val Asp Ile Ala Asp Val Thr
660                 665                 670 cca gag atg aga agt caa gct aaa gca gta aat ttt ggt ata gtt tat    2064
Pro Glu Met Arg Ser Gln Ala Lys Ala Val Asn Phe Gly Ile Val Tyr
        675                 680                 685 ggg att tct gat tat ggt ctt gca agg gat att aaa att tcc agg aaa    2112
Gly Ile Ser Asp Tyr Gly Leu Ala Arg Asp Ile Lys Ile Ser Arg Lys
    690                 695                 700 gaa gct gca gag ttt ata aat aag tat ttt gag cgt tat ccc aaa gtt    2160
Glu Ala Ala Glu Phe Ile Asn Lys Tyr Phe Glu Arg Tyr Pro Lys Val
705                 710                 715                 720 aaa gag tat tta gat aat act gtt aag ttt gct cgt gat aat gga ttt    2208
Lys Glu Tyr Leu Asp Asn Thr Val Lys Phe Ala Arg Asp Asn Gly Phe
                725                 730                 735 gtt ttg act tta ttt aat aga aag aga tat ata aaa gac ata aaa tct    2256
Val Leu Thr Leu Phe Asn Arg Lys Arg Tyr Ile Lys Asp Ile Lys Ser
            740                 745                 750 aca aac aga aac tta agg ggt tat gca gaa agg att gca atg aat tcg    2304
Thr Asn Arg Asn Leu Arg Gly Tyr Ala Glu Arg Ile Ala Met Asn Ser
        755                 760                 765 cca att cag ggc agt gct gct gat atc atg aaa ttg gca atg att aag    2352
Pro Ile Gln Gly Ser Ala Ala Asp Ile Met Lys Leu Ala Met Ile Lys
    770                 775                 780 gtt tat cag aaa ctt aaa gaa aac aat ctc aaa tca aaa ata att ttg    2400
Val Tyr Gln Lys Leu Lys Glu Asn Asn Leu Lys Ser Lys Ile Ile Leu
785                 790                 795                 800 cag gta cac gat gag ctt tta att gaa gcc cca tac gaa gaa aag gat    2448
Gln Val His Asp Glu Leu Leu Ile Glu Ala Pro Tyr Glu Glu Lys Asp
                805                 810                 815 ata gta aag gaa ata gta aaa aga gaa atg gaa aat gcg gta gct tta    2496
Ile Val Lys Glu Ile Val Lys Arg Glu Met Glu Asn Ala Val Ala Leu
            820                 825                 830 aaa gta cct ttg gta gtt gaa gtg aaa gaa gga ctg aac tgg tat gag    2544
Lys Val Pro Leu Val Val Glu Val Lys Glu Gly Leu Asn Trp Tyr Glu
        835                 840                 845 aca aaa tag                                                        2553
Thr Lys
    850

<210> SEQ ID NO 8
<211> LENGTH: 850
<212> TYPE: PRT
<213> ORGANISM: Abedus herberti

<400> SEQUENCE: 8

Met Lys Leu Val Ile Phe Asp Gly Asn Ser Ile Leu Tyr Arg Ala Phe
1               5                   10                  15

Phe Ala Leu Pro Glu Leu Thr Thr Ser Asn Asn Ile Pro Thr Asn Ala
            20                  25                  30

Ile Tyr Gly Phe Val Asn Val Ile Leu Lys Tyr Leu Glu Gln Glu Lys
        35                  40                  45

Pro Asp Tyr Val Ala Val Ala Phe Asp Lys Gly Arg Glu Ala Arg
    50                  55                  60

Lys Ser Glu Tyr Glu Glu Tyr Lys Ala Asn Arg Lys Pro Met Pro Asp
65                  70                  75                  80
```

```
Asn Leu Gln Val Gln Ile Pro Tyr Val Arg Glu Ile Leu Tyr Ala Phe
                85                  90                  95
Asn Ile Pro Ile Ile Glu Phe Glu Gly Tyr Glu Ala Asp Asp Val Ile
            100                 105                 110
Gly Ser Leu Val Asn Gln Phe Lys Asn Thr Gly Leu Asp Ile Val Ile
        115                 120                 125
Ile Thr Gly Asp Arg Asp Thr Leu Gln Leu Leu Asp Lys Asn Val Val
130                 135                 140
Val Lys Ile Val Ser Thr Lys Phe Asp Lys Thr Val Glu Asp Leu Tyr
145                 150                 155                 160
Thr Val Glu Asn Val Lys Glu Lys Tyr Gly Val Trp Ala Asn Gln Val
                165                 170                 175
Pro Asp Tyr Lys Ala Leu Val Gly Asp Gln Ser Asp Asn Ile Pro Gly
            180                 185                 190
Val Lys Gly Ile Gly Glu Lys Ser Ala Gln Lys Leu Leu Glu Glu Tyr
        195                 200                 205
Ser Ser Leu Glu Glu Ile Tyr Gln Asn Leu Asp Lys Ile Lys Ser Ser
    210                 215                 220
Ile Arg Glu Lys Leu Glu Ala Gly Lys Asp Met Ala Phe Leu Ser Lys
225                 230                 235                 240
Arg Leu Ala Thr Ile Val Cys Asp Leu Pro Leu Asn Val Lys Leu Glu
                245                 250                 255
Asp Leu Arg Thr Lys Glu Trp Asn Lys Glu Arg Leu Tyr Glu Ile Leu
            260                 265                 270
Val Gln Leu Glu Phe Lys Ser Ile Ile Lys Arg Leu Gly Val Leu Ser
        275                 280                 285
Glu Val Gln Phe Glu Phe Val Gln Arg Thr Asp Ile Pro Asp Val
290                 295                 300
Glu Gln Lys Glu Leu Glu Ser Ile Ser Gln Ile Arg Ser Lys Glu Ile
305                 310                 315                 320
Pro Leu Met Phe Val Gln Gly Glu Lys Cys Phe Tyr Leu Tyr Asp Gln
                325                 330                 335
Glu Ser Asn Thr Val Phe Ile Thr Ser Asn Lys Leu Leu Ile Glu Glu
            340                 345                 350
Ile Leu Lys Ser Asp Thr Val Lys Ile Met Tyr Asp Leu Lys Asn Ile
        355                 360                 365
Phe His Gln Leu Asn Leu Glu Asp Thr Asn Asn Ile Lys Asn Cys Glu
    370                 375                 380
Asp Val Met Ile Ala Ser Tyr Val Leu Asp Ser Thr Arg Ser Ser Tyr
385                 390                 395                 400
Glu Leu Glu Thr Leu Phe Val Ser Tyr Leu Asn Thr Asp Ile Glu Ala
                405                 410                 415
Val Lys Lys Asp Lys Lys Ile Val Ser Val Val Leu Leu Lys Arg Leu
            420                 425                 430
Trp Asp Glu Leu Leu Arg Leu Ile Asp Leu Asn Ser Cys Gln Phe Leu
        435                 440                 445
Tyr Glu Asn Ile Glu Arg Pro Leu Ile Pro Val Leu Tyr Glu Met Glu
    450                 455                 460
Lys Thr Gly Phe Lys Val Asp Arg Asp Ala Leu Ile Gln Tyr Thr Lys
465                 470                 475                 480
Glu Ile Glu Asn Lys Ile Leu Lys Leu Glu Thr Gln Ile Tyr Gln Ile
                485                 490                 495
Ala Gly Glu Trp Phe Asn Ile Asn Ser Pro Lys Gln Leu Ser Tyr Ile
```

-continued

```
                        500                     505                     510
    Leu Phe Glu Lys Leu Lys Leu Pro Val Ile Lys Lys Thr Lys Thr Gly
                515                     520                     525

Tyr Ser Thr Asp Ala Glu Val Leu Glu Glu Leu Phe Asp Lys His Glu
                530                     535                     540

Ile Val Pro Leu Ile Leu Asp Tyr Arg Met Tyr Thr Lys Ile Leu Thr
    545                     550                     555                     560

Thr Tyr Cys Gln Gly Leu Leu Gln Ala Ile Asn Pro Ser Ser Gly Arg
                            565                     570                     575

Val His Thr Thr Phe Ile Gln Thr Gly Thr Ala Thr Gly Arg Leu Ala
                    580                     585                     590

Ser Ser Asp Pro Asn Leu Gln Asn Ile Pro Val Lys Tyr Asp Glu Gly
                595                     600                     605

Lys Leu Ile Arg Lys Val Phe Val Pro Glu Gly Gly His Val Leu Ile
            610                     615                     620

Asp Ala Asp Tyr Ser Gln Ile Glu Leu Arg Ile Leu Ala His Ile Ser
    625                     630                     635                     640

Glu Asp Glu Arg Leu Ile Ser Ala Phe Lys Asn Asn Val Asp Ile His
                            645                     650                     655

Ser Gln Thr Ala Ala Glu Val Phe Gly Val Asp Ile Ala Asp Val Thr
                    660                     665                     670

Pro Glu Met Arg Ser Gln Ala Lys Ala Val Asn Phe Gly Ile Val Tyr
                        675                     680                     685

Gly Ile Ser Asp Tyr Gly Leu Ala Arg Asp Ile Lys Ile Ser Arg Lys
            690                     695                     700

Glu Ala Ala Glu Phe Ile Asn Lys Tyr Phe Glu Arg Tyr Pro Lys Val
    705                     710                     715                     720

Lys Glu Tyr Leu Asp Asn Thr Val Lys Phe Ala Arg Asp Asn Gly Phe
                        725                     730                     735

Val Leu Thr Leu Phe Asn Arg Lys Arg Tyr Ile Lys Asp Ile Lys Ser
                    740                     745                     750

Thr Asn Arg Asn Leu Arg Gly Tyr Ala Glu Arg Ile Ala Met Asn Ser
                    755                     760                     765

Pro Ile Gln Gly Ser Ala Ala Asp Ile Met Lys Leu Ala Met Ile Lys
            770                     775                     780

Val Tyr Gln Lys Leu Lys Glu Asn Asn Leu Lys Ser Lys Ile Ile Leu
    785                     790                     795                     800

Gln Val His Asp Glu Leu Leu Ile Glu Ala Pro Tyr Glu Glu Lys Asp
                        805                     810                     815

Ile Val Lys Glu Ile Val Lys Arg Glu Met Glu Asn Ala Val Ala Leu
                    820                     825                     830

Lys Val Pro Leu Val Val Glu Val Lys Glu Gly Leu Asn Trp Tyr Glu
                835                     840                     845

Thr Lys
        850
```